(12) United States Patent
Parten

(10) Patent No.: US 6,478,929 B1
(45) Date of Patent: Nov. 12, 2002

(54) DEWATERING PROCESS

(75) Inventor: William David Parten, Stokesley (GB)

(73) Assignee: Lucite International UK Limited, Southampton (GB)

( * ) Notice: Subject to any disclaimer, the term of this patent is extended or adjusted under 35 U.S.C. 154(b) by 0 days.

(21) Appl. No.: 09/701,877

(22) PCT Filed: Jun. 1, 1999

(86) PCT No.: PCT/GB99/01724

§ 371 (c)(1), (2), (4) Date: Jan. 22, 2001

(87) PCT Pub. No.: WO99/64387

PCT Pub. Date: Dec. 16, 1999

(30) Foreign Application Priority Data

Jun. 5, 1998 (GB) .............................. 9812083

(51) Int. Cl.⁷ .............................. B01D 3/34; C07C 45/82
(52) U.S. Cl. .............................. 203/17; 203/57; 203/60; 203/61; 203/99; 203/DIG. 19; 203/DIG. 21; 568/492; 568/493
(58) Field of Search ................ 203/57, 91–92, 203/95–96, 14, 17, DIG. 21, DIG. 19, DIG. 23, 60, 61, 99; 568/492, 493; 562/600

(56) References Cited

U.S. PATENT DOCUMENTS

| 3,174,912 A | 3/1965 | Heinz ......................... 203/62 |
| 3,629,997 A | * 12/1971 | DeMuth ........................ 55/89 |
| 3,994,977 A | * 11/1976 | Aicher et al. ............... 202/158 |
| 4,040,913 A | 8/1977 | Clovis et al. ............... 562/592 |
| 4,348,540 A | * 9/1982 | Ferris et al. ............... 568/472 |

FOREIGN PATENT DOCUMENTS

| FR | 2 409 975 | 6/1979 |
| GB | 130 1533 | 12/1972 |

* cited by examiner

Primary Examiner—Virginia Manoharan
(74) Attorney, Agent, or Firm—Pillsbury Winthrop LLP

(57) ABSTRACT

A formaldehyde-containing product is separated from a formalin solution containing formaldehyde, water and methanol by distilling the solution in the presence of a water entraining compound, especially methyl propionate or methyl methacrylate. The product contains substantially less water than in the solution and may be used, for example, in a further process which requires a source of formaldehyde containing a relatively low level of water, for example, the catalyzed reaction of methyl propionate with formaldehyde and methanol to produce methyl methacrylate.

9 Claims, 1 Drawing Sheet

DEWATERING PROCESS

Figure 1:
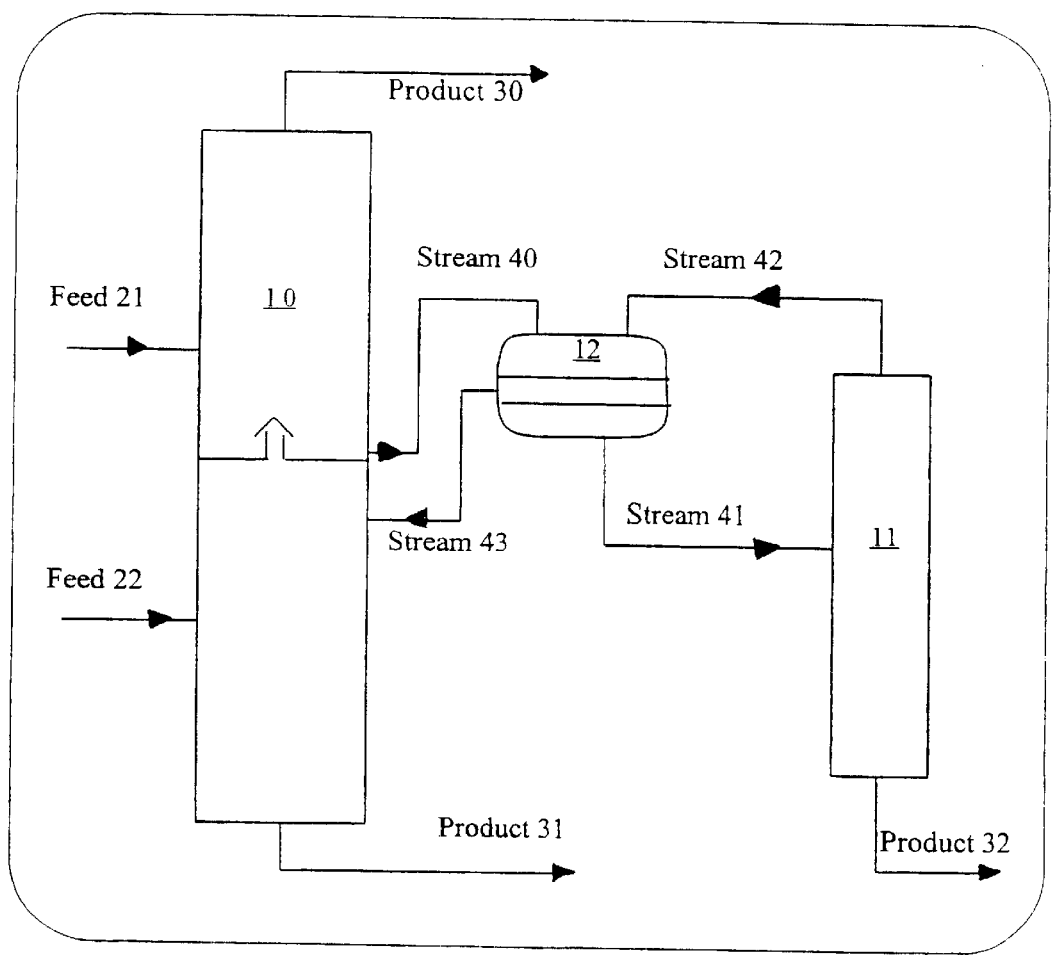

This application is the national phase of international application PCT/GB99/01724 filed Jun. 1, 1999 which designated the US was published in the English language.

The present invention relates to a process for the removal of water from solutions containing formaldehyde for the production of formaldehyde.

Formaldehyde is a commodity chemical that is conveniently produced and transported in the form of formalin solutions. Formalin solutions contain typically between 30% and 60% formaldehyde, the balance of the solution being mostly water, usually with some methanol present. The formaldehyde is predominantly present as complexes with water or methanol in the form of glycols of hemiformals. There are a number of methods described in the patent literature for the dehydration of formaldehyde solutions with the object of producing a dry monomeric formaldehyde stream. For example U.S. Pat. No. 4,962,235 describes the purification of a formaldehyde/water/methanol mixture by distilling in the presence of a polyalkylene oxide such that formaldehyde vapour is produced at the top of the column and polyalkylene oxide, water and methanol are removed from the bottom of the column.

NL-A-6814946 describes a process for recovering formaldehyde from aqueous formaldehyde streams by contacting the stream with $C_6$–$C_{10}$ aliphatic alcohol which reacts with the formaldehyde to form a hemiformal which can be separated from the water and subsequently dissociated back to the alcohol and formaldehyde components.

U.S. Pat. No. 3,174,912 describes a process for the removal of water and coloured organic impurities from a dilute aqueous formaldehyde mixture by distillation in the presence of acetone. A mixed stream containing acetone and formaldehyde and a small amount of water is removed from the top of the column and separated by partial condensation into a stream containing a relatively small amount of formaldehyde in acetone and a stream containing a larger proportion of formaldehyde in acetone.

It is, however, desirable to avoid the introduction of additional chemical compounds into a process which requires purified formaldehyde because the additional compound may need to be removed from the process at a subsequent stage.

One process in which formaldehyde is used is that for the production of methyl methacrylate by the reaction of methyl propionate with formaldehyde in the presence of methanol. The use of formaldehyde as a readily available formalin solution introduces water into the reaction which may have a deleterious effect on the catalyst used and is likely to promote the hydrolysis reactions of the methyl propionate reactant and of the methyl methacrylate product. Water is produced as a by-product of the methacrylate synthesis reaction and it is therefore desirable to reduce to a minimum the amount of water that is introduced into the reaction zone with the feeds so that the level of water in the reactor is maintained as low as possible. Processes for the production of methyl methacrylate, in which propionic acid or its methyl ester is reacted with formaldehyde or methylal in the presence of methanol, are disclosed in U.S. Pat. No. 3,535,371, U.S. Pat. No. 4,336,403, GB-A-1107234, JP-A-63002951. However there is no disclosure in these references of how to prepare the feed materials, particularly the formaldehyde, for the required reaction.

U.S. Pat. No. 4,040,913 discloses the use of water entraining compounds such as benzene, toluene or methylisobutyl ketone, and FR-A-2409 975 discloses the use of saturated $C_4$–$C_6$ hydrocarbons. GB-A-1301533 discloses the use of alkanols being $C_3$–$C_6$ compounds but the alkanols are not used as water entraining compounds.

It is therefore an object of the invention to provide a process for the preparation of a formaldehyde feed product from a formaldehyde-containing solution.

It is a further object of the invention to provide a process for treatment of a formaldehyde-containing solution to yield a formaldehyde feed suitable for use in a methyl-methacrylate production process which contains a reduced amount of water compared to the original formaldehyde-containing solution.

According to the invention, a process for separating a formaldehyde-containing product from a formaldehyde solution comprising formaldehyde, water and methanol, wherein said formaldehyde-containing product contains substantially less water than said formaldehyde solution, comprising distilling said formaldehyde solution in the presence of a water entraining compound.

The water entraining compound is selected such that it is capable of dissolving water, formaldehyde, methanol and hemiformal compounds formed by the reaction of formaldehyde with methanol. The water entraining compound is preferably a saturated or unsaturated carboxylic acid or ester or a carbonyl compound which is substantially unreactive towards formaldehyde under the conditions of the distillation and also able to entrain the water, preferably by forming a minimum boiling azeotropic mixture with water Preferably the water entraining compound forms a heterogeneous minimum boiling azeotrope with water. Suitable compounds include $C_4$–$C_8$ alkanoic acids and their lower alkyl, e.g. $C_1$–$C_8$, esters, and ketones having at least 4 carbon atoms such as diethyl ketone. Particularly preferred compounds are esters and methyl propionate and methyl methacrylate have been found to be especially useful in certain processes. It is greatly preferred to use a compound which is intended to be introduced into a process in which the dewatered formaldehyde product is intended to be used.

One particularly preferred compound for use in dewatering a formalin solution to produce formaldehyde suitable for use in a process to react formaldehyde with methyl propionate in the presence of methanol is methyl propionate. In one preferred form of the invention we therefore provide a process for separating a formaldehyde-containing product from a formaldehyde solution comprising formaldehyde, water and optionally methanol, wherein said formaldehyde-containing product contains substantially less water than said formalin solution, comprises distilling said formaldehyde solution in the presence of methyl propionate.

According to a second aspect of the invention we provide a process for the production of methyl methacrylate by the reaction of formaldehyde with methyl propionate in the presence of methanol and of a suitable catalyst, wherein said formaldehyde is produced from a formaldehyde solution by means of distilling said formaldehyde solution in the presence of methyl propionate. Suitable catalysts are known in the art and include silica catalysts having alkali metal sites.

The process of this aspect of the invention is beneficial, in that formaldehyde feed is recovered as a complex with methanol in a methyl propionate rich stream and water is removed from the process substantially free of organics. Integration of the process for producing formaldehyde of the present invention with a methyl methacrylate producing process as described has the additional advantage that the overall energy requirement for the combined process may be reduced compared with other formaldehyde dewatering methods.

Although we have found that the process of the present invention is particularly suitable to provide a formaldehyde feedstock for subsequent reaction for methyl methacrylate production, the invention is not limited to the production of formaldehyde for such a process and may be suitable to produce dewatered formaldehyde for other applications.

The formaldehyde solution is preferably standard formalin which usually contains water and formaldehyde in approximately equal proportions, usually with a small quantity of methanol. At least some of the formaldehyde is normally present as various water-formaldehyde or methanol-formaldehyde adducts. Normally the term "formaldehyde" will be used here to refer to the total formaldehyde, whether present as free formaldehyde or in the form of such adducts. The composition of formalin solutions may vary and the process of the invention may be operated for a variety of different formalin compositions.

It is preferred that the formaldehyde solution is pre-mixed with methanol before the distillation process. The methanol/formalin mixture is preferably allowed to equilibrate so that formation of methanol-formaldehyde adduct species is promoted, e.g., by allowing the mixture sufficient time to equilibrate, or by stirring or adjusting the temperature of the mixture. Preferably a suitable amount of methanol is used to provide a molar ratio of methanol to formaldehyde of 0.3–1.5:1, more preferably 0.5–1.2:1, especially 0.8–1.1:1. The methanol may be provided in the form of a mixture with methyl propionate, for example to enable recirculated methanol from the distillation or form an associated process or process step to be used.

The amount of water entraining compound introduced into the distillation is in excess of the amount required to form an azeotropic mixture with the water and preferably also with any methanol present so that the water in the mixture is more volatile than the formaldehyde adducts. Methyl propionate forms an azeotropic mixture with water comprising 92% methyl propionate and 8% water. The methyl methacrylate/water azeotrope contains about 14% water (by mass) and the diethyl ketone/water azeotrope contains about 84% diethyl ketone by mass. Preferably the relative proportion of water entraining compound to formaldehyde in the base of the column is in the range 5:1–20:1, e.g. about 10:1 by mass. However, when the water-entraining compound is refluxed, the amount fed to the column may be adjusted as necessary.

The majority of the water is removed as a mixture with the water entraining compound. A stream containing most of the water may be conveniently removed from the distillation process as a liquid sidestream, e.g. by using a chimney tray or similar device at an appropriate position in the column. A suitable position for withdrawing such a sidestream may be determined by considering the composition of the liquid phase throughout the column by known methods in the art. Methyl propionate and water form a heterogeneous azeotrope comprising 92% methyl propionate w/w. This azeotropic mixture may be separated in a decanter and the organic phase thus produced, which comprises mainly methyl propionate may be refluxed into the distillation process. The aqueous phase produced from the decanter may be further treated in a second distillation unit, preferably at elevated pressure, to give an aqueous stream which is largely free of methanol, formaldehyde and methyl propionate. The overheads from the second distillation unit can be recycled back to the main column or to the decanter or to the formaldehyde solution pre-treatment, if present.

Most of the formaldehyde is taken as a bottom product as a mixture with the water entraining compound. This mixture may be used directly if required for a further reaction in which both compounds are used together, e.g. in the synthesis of methyl methacrylate. This formaldehyde-containing mixture contains substantially less water than the formaldehyde solution fed to the process. For example, in a typical process according to the invention using methyl propionate as the water entrainer, a formalin solution containing formaldehyde and water at a weight ratio of approximately 1:1 may produce a dewatered formaldehyde stream containing formaldehyde and water at a weight ratio of about 10:1.

The process of the present invention is preferably carried out in such a way that the purified formaldehyde product may be used in a further process for which it is required. Preferably the process of the present invention is integrated with such a further process so that the purified formaldehyde product is supplied directly to that further process. When the formaldehyde product from the process of the present invention is intended to be used as a feedstock together with the water entraining compound in a further process, e.g. for the production of methyl methacrylate from formaldehyde and methyl propionate when methyl propionate is used as the water-entraining compound, then the process of the present invention and the manufacture of methyl propionate may beneficially be operated in proximity to or integrated with the further process.

In a preferred arrangement, methyl propionate is produced by a process which provides a source of methyl propionate mixed with methanol and, optionally, water. This mixture may be fed to the distillation of the present invention to extract the formaldehyde from a formalin solution. In this way, the separation of the methyl propionate from the process in which it is produced may be avoided. When the feedstocks used contain methanol as described, an azeotropic mixture of methyl propionate and the methanol not complexed with the formaldehyde may be removed from the top of the distillation column. That mixture may be recycled or removed to storage or a further process.

When the formaldehyde from the process of the invention is intended to be reacted with methyl propionate and methanol to produce methyl methacrylate, then the process of the present invention is especially convenient, particularly if used in conjunction with a methyl propionate-producing process as described above. Thus, in a second preferred arrangement, the dewatered formaldehyde mixture with methyl propionate is used, directly or after an intermediate treatment, in such a methyl methacrylate process. Similarly, a methyl propionate—methanol stream, which may be derived from a process to produce methyl propionate, and used in the present invention may also be used to make methyl methacrylate in an integrated process.

One embodiment of the invention will now be further described, by way of example only, with reference to the accompanying drawings FIG. 1, which is a schematic process diagram.

Formalin solution is mixed with methanol and introduced into distillation column 10 as feed 22. Distillation unit 10 includes a chimney tray facility to withdraw some or all of the liquid at a location above feed 22. Above the chimney tray an additional feed, 21, is admitted which includes methanol, water and methyl propionate which may have been derived from a previous process. A sidestream, 40, is removed at the chimney tray which may represent the whole of the liquid flow in the column and phase separated in decanter 12. The organic phase is returned to the column below the chimney tray as stream 43 whilst the aqueous phase is passed to column 11 for further processing as stream 41. Column 10 is typically operated such that the majority of the formaldehyde exits the bottom as stream 31 complexed with methanol, free methanol is removed overhead as its azeotrope with methyl propionate as stream 30 whilst water is removed via the sidestream and decanter system.

Column 11 is operated to drive formaldehyde, methanol and methyl propionate overhead in stream 42 with some water. This is best achieved at elevated pressures typically between 3 and 20 bar. The bottoms product is a clean water stream 31 which can either be reused in the process or removed. Stream 42 is show as being returned to decanter 12 but it could be returned directly to column 11 or mixed with stream 22 and hence recirculated to column 10.

EXAMPLE 1

Formalin consisting of 28.5% formaldehyde, 30.7% methanol and 40.8% water by mass was mixed with methyl propionate such that methyl propionate represented 43.5% by mass of the mixture. This was allowed to stand for several hours so that the mixture equilibrated and was then fed to plate 15 of a 40 plated Oldershaw column, numbering from the bottom upwards, at a rate of 150 ml/h. The column was equipped with a water cooled condenser and a decanter. Pure methyl propionate was added to the decanter of a rate of 360 ml/hr. The organic phase from the decanter was refluxed to the column whilst the aqueous phase was collected and analysed.

90% of the formaldehyde fed was recovered in the stream taken from the bottom of the column and 95% of the water fed was recovered in the aqueous overhead stream. The bottoms stream contained formaldehyde:water in the ratio of 1:0.076 whereas the original formalin contained formaldehyde to water in the ratio of 1:1.4.

EXAMPLE 2

In an example of operating the process of the invention on a continuous basis, formalin solution consisting of 55% water, 35% formaldehyde and 10% methanol was mixed with an azeotropic mixture of methyl propionate and methanol resulting in a mixture containing, by mass, 20% methyl propionate, 23% methanol, 35% water and 22% formaldehyde. The mixture was allowed to stand for at least 12 hours to allow the formaldehyde adducts to equilibrate. The mixture was then fed to stage 30 (counting from the bottom stage) of a 100 stage Oldershaw column at a rate of 18 ml per hour. A second feed containing 86% methyl propionate, 9% methanol, 3% water and 2% formaldehyde was fed to stage 80 of the column at a rate of 162 ml per hour. A sidestream containing the total column liquid flow was taken from stage 60 and fed to a water-cooled decanter where it was allowed to phase separate. The organic phase was returned to the column as a reflux and the aqueous phase was removed.

After operating the column continuously for 12 hours, the total products collected from the top and bottom streams from the column were analysed. The top product from the column was an azeotropic mixture of methanol and methyl propionate. The bottom product from the column contained approx. 0.3% water, 4.75% formaldehyde with the balance being methyl propionate. Therefore the mass ratio of water to formaldehyde had been reduced from 1.57:1 in the formalin solution to 0.06:1 in the bottom column product stream.

What is claimed is:

1. A process for separating a formaldehyde-containing product from a formaldehyde solution comprising formaldehyde, water and methanol, wherein said formaldehyde containing product contains substantially less water than said formaldehyde solution, comprising distilling said formaldehyde solution in the presence of a water entraining compound wherein said formaldehyde solution contains methanol at a molar ratio of methanol to formaldehyde of 0.3–1.5:1.

2. A process as claimed in claim 1, wherein the formaldehyde solution is pre-mixed with a quantity of methanol before the distillation process such that the molar ratio of methanol to formaldehyde is in the range of 0.3–1.5:1.

3. A process as claimed in claim 1, wherein the water entraining compound is selected from the group consisting of a saturated or unsaturated carboxylic acid, an ester and a carbonyl compound.

4. A process as claimed in claim 3, wherein the water entraining compound is methyl propionate or methyl methacrylate.

5. A process as claimed in claim 1, wherein the distilling is carried out in a column wherein the ratio of water entraining compound to formaldehyde in the base of the column is in the range of 5:1–20:1 by mass.

6. A process as claimed in claim 1, wherein a liquid sidestream containing at lest the majority of the water contained in said formaldehyde solution is withdrawn from the distillation process.

7. A process as claimed in claim 1, wherein said process is integrated with a further process so that the formaldehyde-containing product is supplied directly to said further process.

8. A process as claimed in claim 7, wherein said further process is a process for the production of methyl methacrylate.

9. A process for the production of methyl methacrylate by the reaction of formaldehyde with methyl propionate in the presence of methanol and of a suitable catalyst, wherein said formaldehyde comprises a formaldehyde-containing product produced from a formaldehyde solution by means of distilling said formaldehyde solution in the presence of methyl propionate, wherein said formaldehyde solution contains methanol at a molar ratio of methanol to formaldehyde of 0.3–1.5:1 and wherein the formaldehyde-containing product contains substantially less water than said formaldehyde solution.

* * * * *